United States Patent
Falbo, Sr. et al.

(10) Patent No.: US 6,832,399 B2
(45) Date of Patent: *Dec. 21, 2004

(54) BREAST BIOPSY BED

(76) Inventors: Michael G. Falbo, Sr., 7300 N. Harrison, Gladstone, MO (US) 64119; Kerry O'Rourke, 12328 W. 100th St., Lenexa, KS (US) 66215

(*) Notice: Subject to any disclaimer, the term of this patent is extended or adjusted under 35 U.S.C. 154(b) by 0 days.

This patent is subject to a terminal disclaimer.

(21) Appl. No.: 10/024,076

(22) Filed: Dec. 17, 2001

(65) Prior Publication Data

US 2002/0056161 A1 May 16, 2002

Related U.S. Application Data

(63) Continuation-in-part of application No. 09/712,475, filed on Nov. 14, 2000, now Pat. No. 6,367,104.

(51) Int. Cl.[7] ................................................. A61B 6/04
(52) U.S. Cl. ........................ 5/601; 5/81.1 HS; 5/611; 378/209
(58) Field of Search ........................... 5/601, 81.1 HS, 5/611, 81.1; 128/922; 378/209

(56) References Cited

U.S. PATENT DOCUMENTS

| | | | |
|---|---|---|---|
| 2,834,030 A | * | 5/1958 | Jones .......................... 5/86.1 |
| 3,428,307 A | * | 2/1969 | Hunter et al. .................. 5/601 |
| 3,635,461 A | | 1/1972 | Bellucci et al. |
| 3,786,523 A | * | 1/1974 | Sele ............................. 5/87.1 |
| 3,997,926 A | | 12/1976 | England |
| 4,761,000 A | | 8/1988 | Fisher et al. |
| 4,769,584 A | | 9/1988 | Irigoyen et al. |
| 4,953,245 A | * | 9/1990 | Jung ............................ 5/86.1 |
| 5,131,105 A | | 7/1992 | Harrawood et al. |
| 5,205,004 A | | 4/1993 | Hayes et al. |
| 5,609,152 A | * | 3/1997 | Pellegrino et al. .......... 600/429 |
| 5,803,913 A | * | 9/1998 | Khalkhali et al. .......... 600/407 |
| 6,367,104 B1 | * | 4/2002 | Falbo et al. .................... 5/601 |

OTHER PUBLICATIONS

What is a Solenoid?, http://www.detroitcoil.com/whatis.htm, Aug. 23, 2001 p. 1–2.
What is a Solenoid?, http://www.detroitcoil.com/whatis2.htm Aug. 23, 2001 p. 1–2.
What is a Solenoid?, http://www.detroitcoil.com/whatis3.htm Aug. 23, 2001 p. 1–2.
What is a Solenoid?, http://www.detroitcoil.com/whatis4.htm Aug. 23, 2001 p. 1–2.
What is a Solenoid?, http://www.detroitcoil.com/whatis5.htm Aug. 23, 2001 p. 1.

* cited by examiner

Primary Examiner—Michael F. Trettel
(74) Attorney, Agent, or Firm—Shughart Thomson & Kilroy P.C.

(57) ABSTRACT

An apparatus and method is provided for accurately positioning a breast tumor of a patient in the decubitus position on examination table and preventing patient movement once the tumor is positioned and for preventing pain and loss of sensation in the patient's downwardly positioned arm and shoulder while the patient is in the decubitus position.

13 Claims, 3 Drawing Sheets

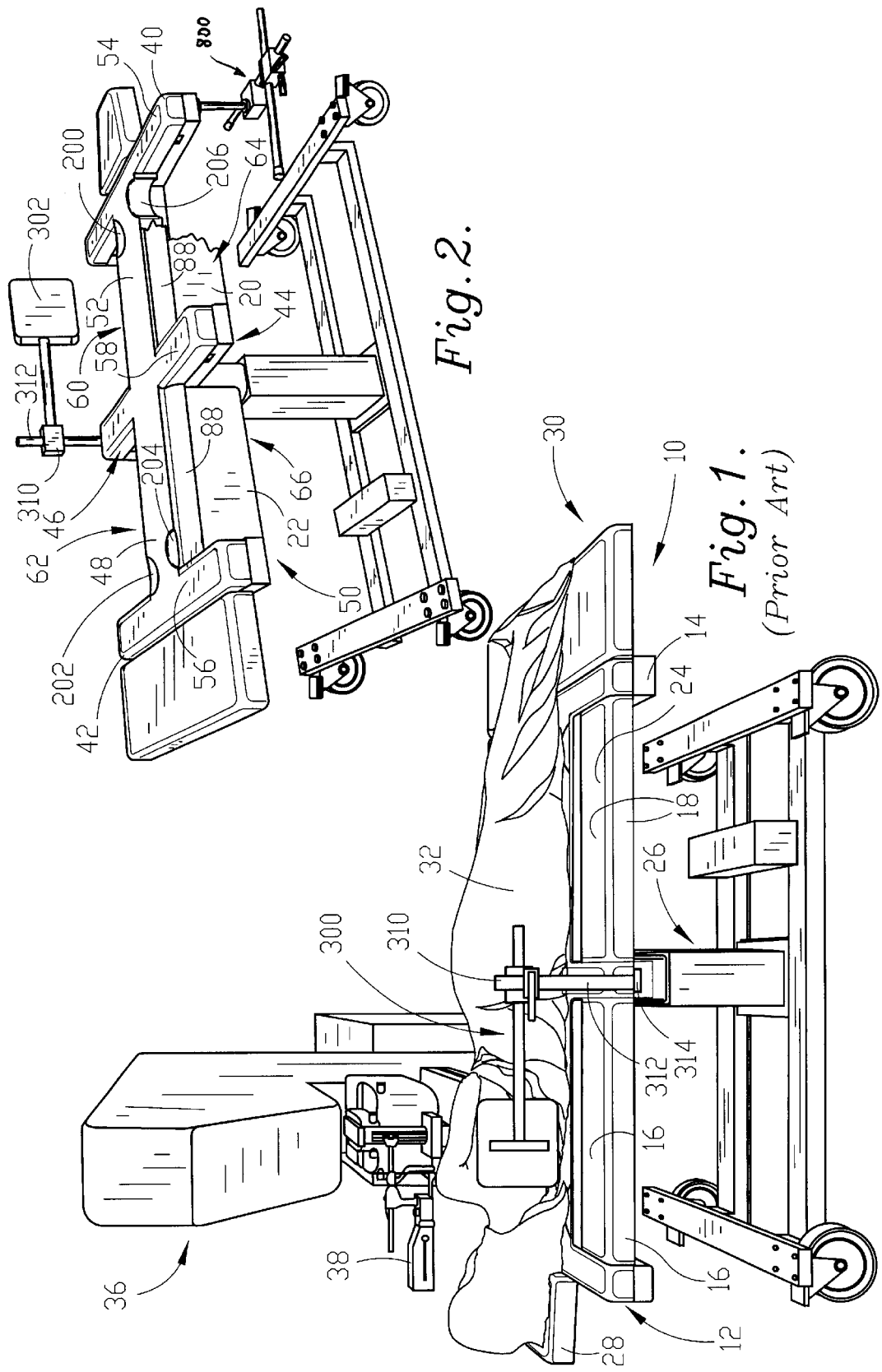

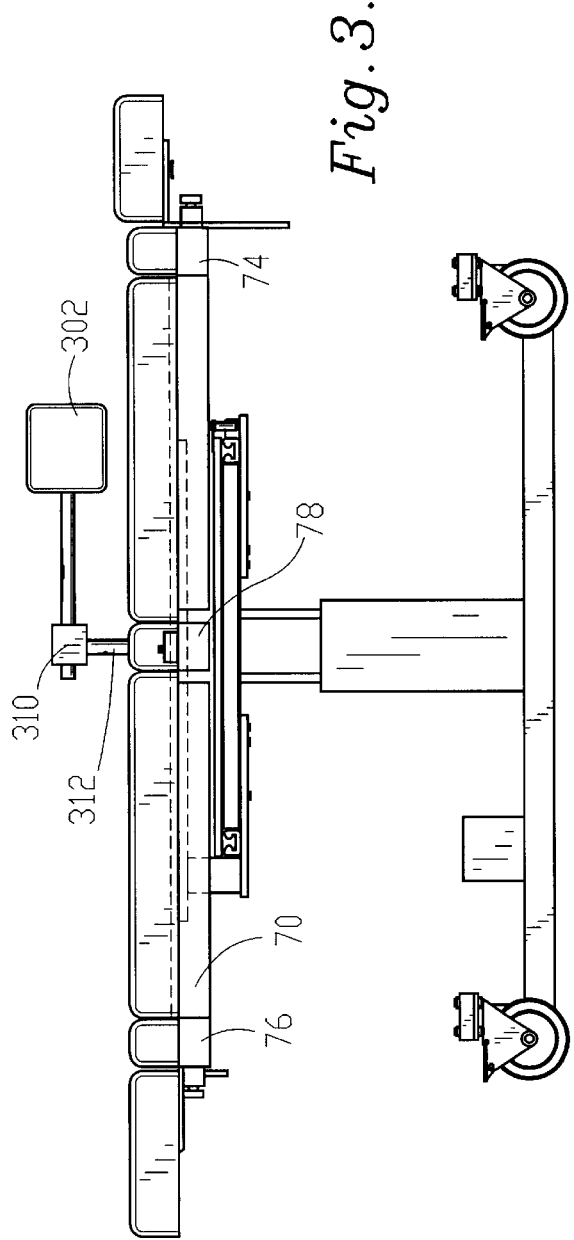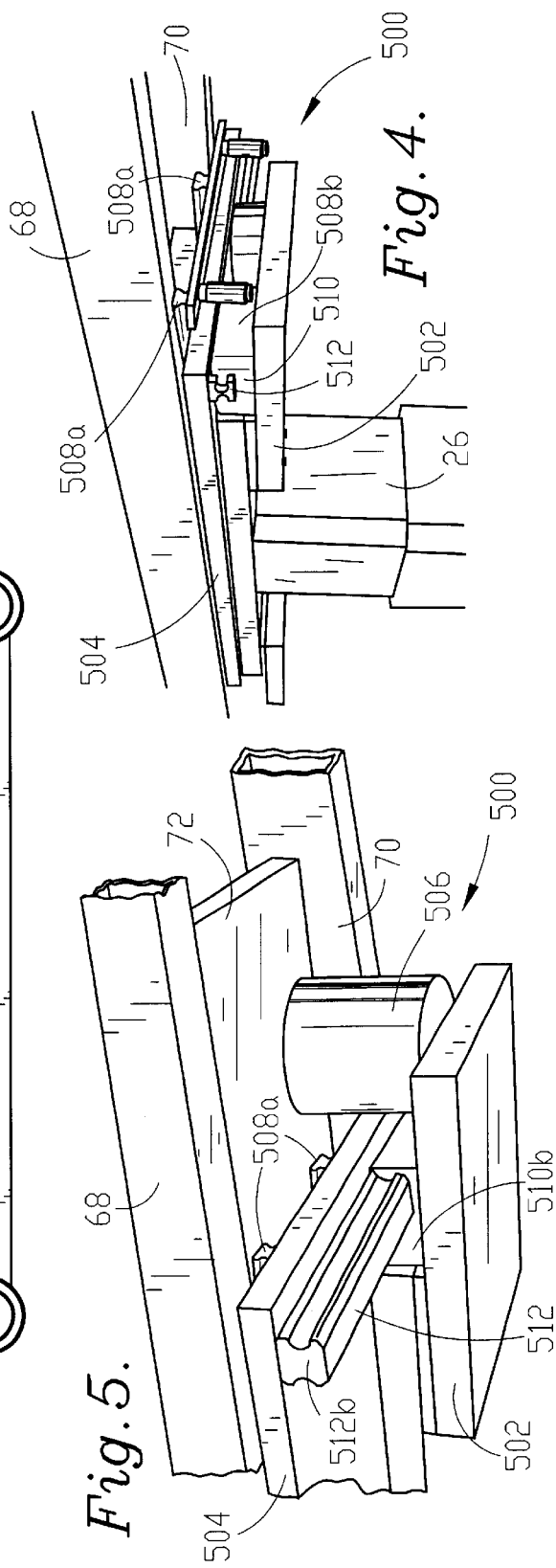

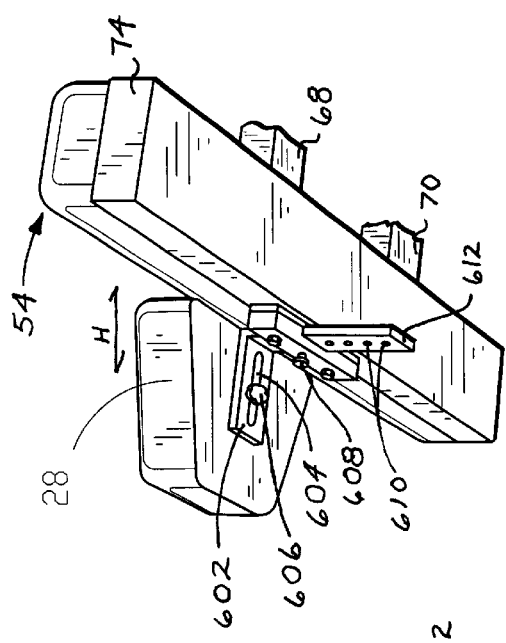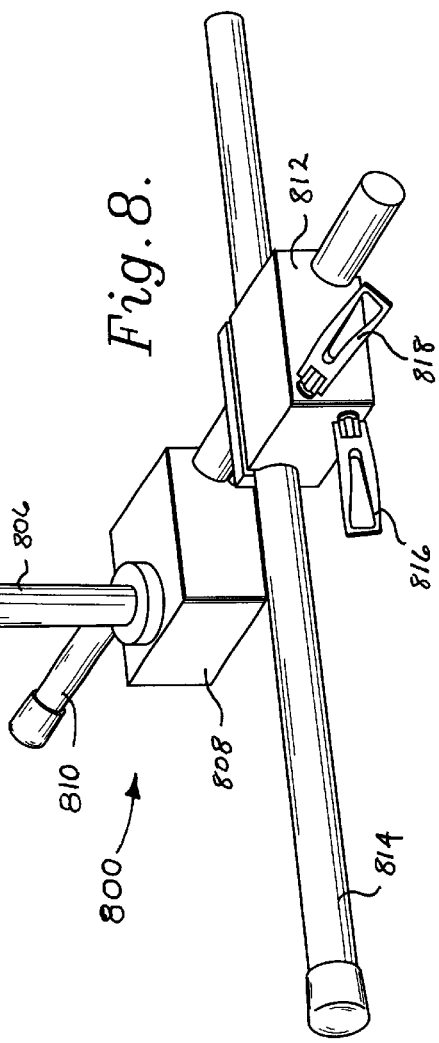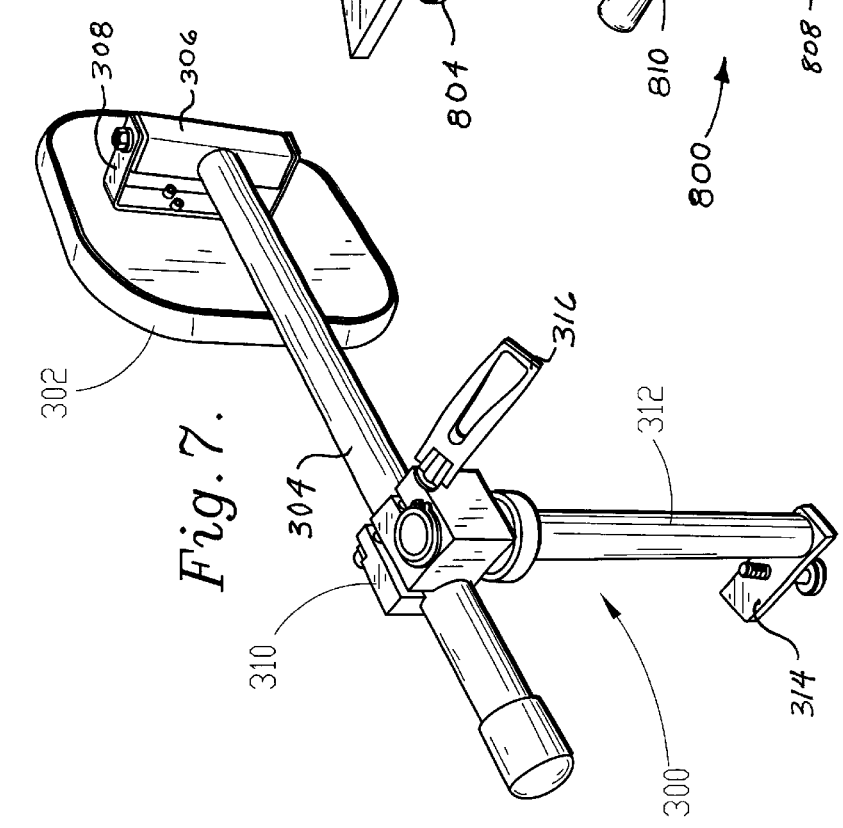

US 6,832,399 B2

BREAST BIOPSY BED

This application is a continuation-in-part application of application Ser. No. 09/712,475 filed Nov. 14, 2000, now issued as U.S. Pat. No. 6,367,104 the specification of which is incorporated herein by reference.

FIELD OF THE INVENTION

The present invention relates to a support apparatus for performing mammograms and breast biopsies during which the patient is in the decubitus position. More specifically, the present invention provides an apparatus and method for accurately repositioning a patent, maintaining the patient in the selected position for breast biopsy and preventing discomfort to the patients bottom arm and shoulder which are supporting the patient's weight during mammography performed in the decubitus position.

BACKGROUND OF THE INVENTION

Advances in the field of mammography have enabled early detection and treatment of cancerous and precancerous tissues. When a mammogram is taken, it is analyzed by a radiologist. If suspicious images are found, a biopsy of the tissue is taken. Mammography typically has been performed with the patient in the standing position, and the breast positioned between two opposed plates which flatten the tissue and hold it in place. If suspicious tissue was observed in the mammogram the physician marked the precise area to be biopsied and a tissue sample was obtained. The procedure of marking the area for biopsy involved inserting a needle into the breast, and feeding of a wire through the needle which remains in place until the biopsy is performed.

In an improved method for performing breast biopsies, known as the core biopsy technique, the patient is placed in a standing or upright sitting position and the biopsy is taken by positioning the patient's breast between the opposed plates of a mammography device. Then, using a medical instrument known as a "breast tissue sampler," a core of tissue is cut at the position indicated by the mammogram. This procedure represents a significant advance, in that the patient is not required to remain with a wire projecting from her breast or move to a remote location for the surgical biopsy. Instead, the biopsy can be performed in the same location as the initial mammogram.

However, during the performance of the core biopsy, it is possible for the patient to move slightly, or worse to faint. Either reaction presents significant problems both for the patient and the technician or radiologist. In one instance a sample from the wrong area is taken, and in the other an incorrect sample can be taken and the patient can be injured by falling. One solution to this problem is to support the patient during core breast tissue sampling by using an examination table having a central, surrounded and not laterally accessible opening therein. With such an examination table, the patient lies in a prone position with her breasts hanging downwardly through the opening. This type of support table is known as a "prone table" or "Parker table." The Parker table is large and not readily repositionable, making access to the breast region difficult. The Parker table also presents a problem in attempting to locate tumors when the patient is small breasted or the suspected tumor is adjacent the chest wall, i.e., the rib cage area.

Thus it would be beneficial if the patient could have mammograms, needle localizations and core biopsies performed when lying on her side. This is known as the decubitus position, wherein the patient's breast is oriented toward the mammogram—preferably with the upper breast positioned for mammography or biopsy, but sometimes with the lower breast examined. The patient may thus be positioned in a left lateral decubitus (left side of patient down) or right lateral decubitus (right side of patient down) to present her breast to for examination. This may require the patient to position her head at either end of the support, or to rotate longitudinally (with feet and head remaining at the same relative ends of the bed) to present the breast in the proper position. The patient must be adequately supported and this support must be provided without giving the patient a sense of anxiety about falling off the support. Additionally, the support must permit access by the technician and access to the mammography and core biopsy machine to enable performance of the mammogram and/or biopsy procedure.

Prior art patient supports are perhaps best shown in U.S. Pat. Nos. 5,184,363 and 5,461,739 to Falbo, Sr., and 5,950,262 to Smoler et al., the disclosures of which are incorporated herein by reference. Such supports are beneficially configured with drop-out sections to permit access by the technician to the patient. However, these patient supports are not configured to meet the peculiar demands of decubitus breast mammography and biopsy. For example the U.S. Pat No. 5,184,363 patent discloses a support bed useful for cardiac sonography having two drop-out sections, the first to permit sonographic diagnosis of a patient lying on the bed, the second to accommodate the legs or other aspect of a person performing the diagnosis. However, the openings do not admit access by a mammography and core biopsy device, nor is the table particularly configured to permit alternate positioning of the patient on either the left or right side. Moreover, a mammography device often must be tilted in which case a bulky portion of the device must lie adjacent the patient's head and below the top surface of the table, which is not possible with the aforementioned support bed. The U.S. Pat. No. 5,461,739 support apparatus is also designed for performing cardiac sonography, but with the patient in a supine position (resting on the back) and accommodating a pedaling device. It also teaches the use of one, or alternatively two, patient drop-out, sections, but is not configured to admit into the openings a mammography and core biopsy device, nor to allow the patient to rest in a variety of different positions to present the breast for examination.

A bed or examination table which allows the patient to be positioned on her side is the subject of U.S. patent application Ser. No. 09/712,475. This patent application teaches the use of an examination table or bed in which the patient may be positioned in a left lateral decubitus or right lateral decubitus position to present her breast for examination and biopsy. While the bed or table of U.S. patent application Ser. No. 09/712,475 provides substantial benefits to the patient, additional improvements and embodiments of the examination table or bed have been discovered which can further increase patient comfort while in the decubitus position, and which can increase the accuracy of the biopsy procedure.

It will be appreciated by those skilled in the art that while a patient is in the decubitus position (FIG. 1) that the patient is able to roll forward and backward on the examination table. Such a forward or backward rolling movement could remove the area of the breast to be biopsied from the field of the biopsy needle. Further, it will be appreciated that the entry of a biopsy needle into the breast and the withdrawal of the needle is a procedure offering discomfort to the patient. This discomfort and the anticipation of it can cause a patient to shift position and even slightly pull away from the biopsy device. This can result in inaccurate biopsy procedures and the need to reperform the unpleasant procedure. Therefore a means for bracing the patient and reducing patient movement while in the decubitus position would greatly benefit the biopsy procedure.

An additional embodiment of the examination table or bed of U.S. patent application Ser. No. 09/712,475 is provided in the present application and which reduces or eliminates the discomfort caused to a patient from being positioned in the left lateral decubitus or right lateral decubitus position for a period of time. While in the left lateral decubitus or right lateral decubitus position much of the patient's weight is resting on the patient's downward arm and shoulder. If the patient is required to remain in the lateral decubitus position for a time the patient can experience pain or the local loss of feeling in the arm or shoulder which is in contact with the examination table. Therefore, a means for reducing the pressure of the patient's body weight on the patient's downward arm and shoulder would be beneficial.

A further problem associated with positioning a patient in either the left lateral decubitus or right lateral decubitus position occurs when a removable filler panel as described in U.S. patent application Ser. No. 09/712,475 is removed and the patient attempts to allow their arm to drop below the surface of the table. In this instance the patient's arm is simply left to dangle downwardly and can contribute to the patient feeling unstable and can contribute to a tendency for the patient to roll forward into the mammography or biopsy device. Therefore, it would be beneficial if an examination table which allows the patient to be positioned in the left or right lateral decubitus positions were to provide a stabilizing means for the patent while the patient's arm is hanging below the table surface.

Yet another advantage could be obtained for the radiologist or technologist using the device of U.S. patent application Ser. No. 09/712,475 if a limited degree of movement of the patent's breast in the lateral plane—a plane parallel to the surface of the bed or table—could be achieved. In a biopsy procedure it may be necessary to take a biopsy from more than one location in a breast, or it may be necessary to shift a patient to place the area to be biopsied more centrally under the biopsy needle. In these cases, presently, the radiologist or technologist must either adjust the position of the patient by directing the patient to move their body slightly, or by readjusting the breast within the biopsy device, or by repositioning the biopsy device. These options do not provide the radiologist or technologist with the fine degree of control which would be beneficial in achieving biopsy accuracy. Therefore it would be of great benefit to a radiologist or technologist if a means were available which would allow the repositioning of a patient, or patients breast with respect to a breast biopsy device.

A further problem is associated with examination tables which position a patient in the left or right lateral decubitus position. If the patient is short in stature, the patient's head will not extend to the end of the table where it can be supported at a different level of height from the table surface. In such cases the patient cannot be shifted toward the headrest as then the patient would not be aligned with the filler section openings. Therefore, it would be beneficial if a headrest for use with left or right lateral decubitus position breast biopsy examination tables were known which would allow the head of a short patient to be supported at a level above the height of the examination table surface.

SUMMARY OF THE INVENTION

These needs have largely been achieved by the method and apparatus of the present invention which in one embodiment provides a method and apparatus of bracing the patient to prevent forward and rearward movement of the patient with respect to a core biopsy device and which in another embodiment provides a method and apparatus for reducing the pressure placed on the downward arm and shoulder of a patient while in the decubitus position and which in another embodiment provides a method and apparatus for adjusting the position of a patient and/or the patient's breast, while the patient is in the decubitus position.

The method and apparatus of bracing the patient to prevent forward and rearward movement of the patient with respect to a core biopsy device comprises the bracing of a patient's rear shoulder area by positioning of a pad against the patient's upper back and shoulder area to prevent rearward movement and to provide a reference point for the patient to press against to assist in preventing forward rolling movement of the patient.

The method and apparatus for reducing the pressure placed on the downward arm and shoulder of a patient while in the decubitus position comprises the provision of a recess or depression in the examination bed or table adjacent the location of the patient's shoulder on the examination table. This recess or depression allows the patient to extend the arm downwardly and to shift the patient's body weight from the downward arm and shoulder and onto the patient's chest wall area.

The method and apparatus for providing a stabilizing means for the patient while the patient's arm is hanging below the table surface comprises a patient support which can be grasped by the patient's downwardly hanging arms and which allows the patient to hold themselves in position and prevent forward rotation of their body toward the biopsy or mammography apparatus while providing the patient with a sense of security and control over their body position.

The method and apparatus for adjusting the position of a patient and/or the patient's breast, while the patient is in the decubitus position comprises the mounting of the table frame on a system of dual, laterally shifting support surfaces which are independently moveable with respect to one another. The surfaces are positioned between the table frame and the upright support and, when released either separately or together, allow a user to shift the table and a patient thereon in two degrees of movement. The two degrees of movement allow movement in all direction in a plane which is parallel to the surface of the examination table. Once the patient is properly repositioned the table surface can be locked into position for the procedure.

The method and apparatus for supporting the shorter patient's head comprises a frame for use with a head support, the frame allowing the head support cushion to be shifted along the longitudinal axis of the examination table to allow the head support to be moved inwardly of the examination table frame to allow positioning of the head support under the head of the shorter stature patient.

The foregoing and other objects are intended to be illustrative of the invention and are not meant in a limiting sense. Many possible embodiments of the invention may be made and will be readily evident upon a study of the following specification and accompanying drawings comprising a part thereof. Various features and subcombinations of invention may be employed without reference to other features and subcombinations. Other objects and advantages of this invention will become apparent from the following description taken in connection with the accompanying drawings, wherein is set forth by way of illustration and example, an embodiment of this invention.

DESCRIPTION OF THE DRAWINGS

Preferred embodiments of the invention, illustrative of the best modes in which the applicant has contemplated applying the principles, are set forth in the following description and are shown in the drawings and are particularly and distinctly pointed out and set forth in the appended claims.

FIG. 1 is a rear perspective view of a patient on the support apparatus of the present invention and showing a patient prepared for mammography in a left lateral decubitus position with the back brace of the present invention in place to prevent the patient from rolling back and away from the biopsy apparatus;

FIG. 2 is a front perspective of the apparatus of FIG. 1 with the patient removed to more clearly show the back brace of the present invention and to also show the four indents adjacent the four access openings in the support apparatus to accommodate a patients downwardly positioned shoulder and arm when the patient is in the decubitus position;

FIG. 3 is a front elevational view of the support apparatus showing the back brace and head support devices and showing the four-way repositioning device of the present invention mounted between the frame and the support pedestal;

FIG. 4 is an enlarged, fragmentary front and right side perspective view of the repositioning device of FIG. 3;

FIG. 5 is an enlarged, fragmentary rear and left side perspective view of the repositioning device of FIG. 3 and showing the electromagnet which locks the bed in the selected position;

FIG. 6 is a bottom perspective view of the head support device of the present invention;

FIG. 7 is a rear perspective view of the back brace device of the present invention and also showing the similarly structured components which comprise the hand brace or hand support of the present invention; and FIG. 8 is a perspective view of the hand brace of the present invention which can be grasped by the hand of the patient's hanging arm.

DESCRIPTION OF THE PREFERRED EMBODIMENT

As required, detailed embodiments of the present inventions are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring now to the FIG. 1, a patient support apparatus 10 for use in the performance of mammography and breast biopsy broadly includes a deck 12, the deck 12 including a frame 14, a multiplicity of filler sections 16, 18, 20 (FIG. 2) and 22 (FIG. 2), and a pad 24 overlying the frame 14 for cushioning the patient thereon. Deck 12 is elevated above the floor or other supporting surface by a deck support 26. Head support 28 and a foot support 30 may be coupled to respective ends of the deck 12. Patient support apparatus 10 is sized to support an adult human patient 32. Patient support apparatus 10 is especially configured for supporting the patient to permit her to present her breast to a mammography device 36 to which a breast tissue sampler 38 maybe attached. Device 36 is positioned in an access site that is provided within the deck 12 when one or more of filler sections 16, 18, 20 or 22 is shifted or removed, thereby enabling patient 32 to be supported by apparatus 10 with the breast in an optimum position for imaging by the device, as shown in FIG. 1.

While multiple embodiments are shown of the present invention, it is to be understood that all are sized and configured to support a human patient thereon, and to accommodate a mammography device and mammotome or an examiner or other member of the technical staff during mammography, needle localization or obtaining a tissue sample. Thus, while patient 32 and device 36 are shown only in FIG. 1, each embodiment of apparatus 10 is adapted for supporting the patient and use with the device.

In FIG. 2, deck 12 is configured with a first end 40 and an opposite second end 42, a first preferably linear side 44, an opposing second preferably linear side 46, a top surface 48 and a bottom surface 50. A longitudinal spine 52 extends between the first and second ends and is preferably centered between the first and second sides. Deck 12 further includes a first outer support arm 54 adjacent the first end 40, a second outer support arm 56 adjacent the second end 42, and a central support arm 58 positioned intermediate the arms 54 and 56. Support arms 54, 56 and 58 are preferably oriented perpendicular to the spine 52, and together define four recesses extending inwardly from the sides 44 and 46 to provide openings 60, 62, 64 and 66 which may receive therein respective filler sections 16 (FIG. 1), 18 (FIG. 1), 20 and 22.

In FIG. 3, frame 14 includes a framework of, preferably, metal, tubular channels including longitudinally extending substantially parallel rails 68 (FIG. 5) and 70 interconnected by plate 72 (FIG. 5), first and second end cross-channels 74 and 76, and center cross-channel 78. Rails and cross-channels thus provide stiffness and support for the spine and arms as a part of the deck 12. The tubular channels are interconnected by welding or mechanical fasteners whereby the channels 74, 76 and 78 are oriented perpendicular to rails 68 and 70 as shown in FIG. 3.

Still referring to FIG. 3, and as more fully discussed in U.S. patent application Ser. No. 09/712,475, which is incorporated herein by reference, a rigid panel of wood, plastic, metal or other substantially rigid material 77 is attached to and overlies the rails 68 (FIG. 5) and 70 (FIG. 5) and cross-channels 74, 76 and 78. The panel serves both to support the pad 24 and rigidify the deck 12. The panel is shaped and sized to provide the four openings 60, 62, 64 and 66 and to receive the filler sections 16, 18, 20 and 22 therein. Each opening most preferably being at least about 18 inches and more preferably about 22 inches or greater longitudinally and preferably about 10 inches across in order to accommodate a currently available mammography device or an examiner therein. Each opening 60, 62, 64 and 66 thus defines an access site for the mammography device 36, examiner or patient. Although only one, two or three openings may be provided in the apparatus 10, the openings 60, 62, 64 and 66 are preferably located so that two openings are located along each side to permit access, and in substantially opposed pairs so that opening 60 is opposite opening 64 and opening 62 is across from opening 66. Each pair of openings is thus preferably separated by spine 52 and the openings along each side are preferably separated by central support arm 58. The filler sections 16, 18, 20 and 22 are sized to be complementarily received in the respective openings 60, 62, 64 and 66.

The filler sections may be configured to be removably coupled to the frame 14. In a preferred embodiment, however, the filler sections are pivotally mounted to the frame and provide access from the sides 44 and 46. To that end, each filler section 16, 18, 20 and 22 includes a sheet of the rigid material 77 previously described for overlying the rails 68 and 70 and cross-channels 74, 76 and 78. Rigid material 77 is covered with a cushion of foam cushioning or the like, covered with fabric, leather, or vinyl cloth. The cloth covering of each filler section 16, 18, 20 and 22 is slightly overlapped by a panel or web 88 of similar material, as shown in FIG. 2. Such a panel or web is shown as reference character 82a in U.S. Pat. No. 5,184,363, the disclosure of which is incorporated herein by reference. Each filler section 16, 18, 20 and 22 is pivotally connected to the frame 14 by a hinge 90, preferably but not necessarily oriented for pivoting on a longitudinally extending axis. Each filler section 16, 18, 20 and 22 further includes a release mechanism which permits filler section 16, 18, 20 and 22 to pivot downwardly to provide opening 60, 62, 64 and 66.

Referring now to FIGS. 1 and 2 deck 12 includes pad 24 is shaped and configured to overlie the frame 14 for supporting the patient 32 on spine 52 and supporting arms 54, 56 and 58 of the deck 12. The pad includes a foam cushion and a cover of the same material as the cloth covering the filler sections. By being superposed relative to the frame 14, the pad 24 provides both cushioning and support for the human patient 32 resting thereon, and positions the patient 32 on a relatively flat, cushioned, horizontal surface across the deck 12 including those areas over the filler sections as wells as the areas above the frame 14.

Deck support 26 elevates the deck 12 above a floor or other supporting surface and preferably includes a base 112 provided with lockable wheels 114 for permitting the entire patient support apparatus 10 to be easily moved or maintained in place as shown and described in U.S. Pat. No. 5,950,262, the disclosure of which is incorporated herein by reference. Thus, the apparatus may rotate about a central, upright axis, translate to carry the patient therewith, and be locked in position against movement by engaging the locking arms of the wheels 114.

The apparatus 10 is configured to accommodate use with a wide variety of mammography devices which comprise one preferred environment of use. The mammography device 36 as illustrated in FIG. 1 is a Model Senovision by General Electric Medical Division of Milwaukee, Wis. It is one example of a device 36 useful herewith and may include an integrated breast tissue sampler 38 positioned adjacent the breast compressing plates of the mammography device 36 for performing core biopsies or needle localizations while the breast of the patient 32 is imaged. One breast tissue sampler 38 which may be mounted on a mammography device 36 for performing core biopsies in accordance with the present invention is a Biopsys device manufactured by Ethicon Endo-Surgery, Inc. of Cincinnati, Ohio and sold under the trademark Mammotome.

In the method of the present invention, patient 32 is positioned on patient support apparatus 10 so that her torso and legs are supported on the portion of the spine 52 with her head resting on the head support 28 and her feet supported either by the foot support 30 or, in shorter patients, by the spine 52 or the filler sections 18 and 20. Any of the filler sections 16, 18, 20 and 22 may be initially raised and locked in position to fill the corresponding openings 60, 62, 64 and 66, so that when the patient moves onto the support apparatus 10 she has good support and a feeling of security during positioning thereon. Apparatus 10 also permits the patient to be supported by the cross-channels and one or more of the filler sections 16, 18, 20 and 22 when that filler section is in a closed position. FIG. 1 shows apparatus 10 and device 36 arranged to receive a patient 32 in a left lateral decubitus position, whereby the image of the patient's upper (right) breast 34 would be achieved from a camera above the right shoulder to the film cassette (not shown) at the patient's midline, a lateral-medial view. Once the patient 32 is in the decubitus position, as shown in FIG. 1 and preferably over the center or spine 52 of the support apparatus 10, one or more of the filler sections 16, 18, 20 or 22 may be dropped to the position shown on the right of FIG. 6 to provide access into that opening by the mammography device 36. For example, as shown in FIG. 1, the filler section 20 would be dropped to clear opening 64 to receive the device 36.

However, support apparatus 10 also permits patient 32 to be positioned to the side of the spine 52, whereby her torso spans an opening in order to place her breast 34 in position for mammography, needle localization or breast biopsy. For example, in order to place the patient in sufficient proximity to the mammography device 36, it may be necessary for the patient to move laterally on the support apparatus so that her hips are over the central support arm 58 and her shoulders supported by one of the outer support arms 54 or 56 depending or her positioning on the apparatus 10, with a filler section dropped to clear the corresponding opening so that some or all of the patient's torso spans that opening. While the apparatus 10 may be used with the patient 32 in a sitting position, more preferably the patient is positioned in either a left decubitus or right decubitus position.

The patient's breast 34 is then placed between the clamping plates adjacent the film cassette of mammography device 36. A better image may often be obtained by imaging the upper breast, and so in the left decubitus position shown in FIG. 1, head support 28 is positioned at first end 40 and foot support 30 at second end 42, with the head support 28 vertically adjusted to be slightly above the upper level of the pad 24 for comfort. Filler section 20 is pivoted downwardly to receive the mammography device 36 in the cleared opening 64. The right breast 34 of the patient 32 is then positioned between the clamping plates of the mammography device 36 for imaging with the breast compressed side to side and the image obtained lateral to medial.

As previously mentioned, when a patient is in the right or left decubitus position, the patient is lying on her side. In this position the downward arm is just in front of the patient and a substantial part of the patients weight is placed on the downward shoulder. Referring to FIG. 1, a patient is shown in the left decubitus position. This patient will have a substantial potion of her upper body weight resting on her downward, or left shoulder. A patient must maintain this position for a number of minutes while the radiologist or technician prepares the mammography device 36 and then prepares and positions the biopsy device 38. During this time the patient is requested to lie as still as possible and to hold the same position between the time mammography is used to locate the area for biopsy and the time the biopsy needle extracts the tissue sample.

This need to remain in one position with a substantial amount of body weight on the shoulder frequently becomes quite uncomfortable for the patient. It is not uncommon for the patient to loose feeling the downward shoulder or arm during periods of lying in the right or left decubitus position. The present invention solves this problem by redistributing some of the patient's weight from resting on the patient's shoulder and shifting the weight to resting on the patients chest. This is accomplished by providing an indent or crescent-shaped depression in the rigid material or panel 77(FIG. 3) of wood, plastic or metal that is mounted on spine 52 with the indent also being formed in rail 68, 72 and in the foam padding and cover material. Indent 200, 202, 204, 206 in spine 52 is adjacent first and second outer support arms 54, 56.

Referring now to FIG. 2, indents 200, 202, 204 and 206 are shown with indents 200, 202, and 204 shown covered with a layer of foam or other padding and a layer of fabric, vinyl or other covering material. Indent 206 is shown with the covering material and the foam padding removed and with a corner of filler section 20 and cover or web 88 removed to reveal the indent formed into rigid material or panel 77(FIG. 3) the wood or metal support covering spine 52 and the indent also being formed in rail 68, 70.

The inclusion of Indent 200, 202, 204, 206 in panel 77 and rail 68, 70 eliminates the structural barrier and allows the patient to drop her arm off the edge of spine 52 so the arm may hang downwardly and out-of-the-way. This repositioning of the arm permits the patient's weight to be distributed between the shoulder and the patient's side chest wall. When a patient attempts to drop their arm off the edge of spine 52, in the absence of indent 200, 202, 204, 206, the patient's arm encounters the hard edge of rigid material 77 and rail 68, 70 near the armpit. This edge is quite uncomfortable for the patient and presents an unsatisfactory option for removing the weight from the patient's downward shoulder and arm. With indents 200, 202, 204, 206 in place a patient can comfortably allow their arm to hang-off the edge of spine 52 during the mammography and biopsy procedure while allowing their shoulder and downward chest wall to support the weight of their upper body.

Referring now to FIG. 2, apparatus 800 for providing a stabilizing means for the patent while the patient's arm is hanging below the table surface will be discussed. To provide the patient with a support to grasp with the patient's downwardly hanging arm a support 800 is provided near the patient's downward arm. Support 800 allows the patient to hold themselves in position and prevent forward rotation of their body toward the biopsy or mammography apparatus while providing the patient with a sense of security and control over their body position.

Referring now to FIG. 8, support 800 will be described in detail. Support 800 is comprised of a support plate 802 which can be secured to the underside ends of support arms 54, 56 and 58. Support plate 802 is secured using thumbscrew 804. Extending downwardly from support plate 802 is vertical rod 806 which is captured at its lower end in two-way compression clamp 808. Also captured in compression clamp 808 is horizontal rod 810. Compression clamp 808 releasably captures vertical rod 806 and horizontal rod 810 to allow rapid changing of the vertical position of horizontal rod 810 within compression clamp 808. Attached to horizontal rod 810 is second two-way compression clamp 812. Two-way compression clamp 812 releasably captures hand-hold rod 814 to allow repositioning of hand-hold rod 814 along horizontal rod 810. Two-way clamps 808, 812 allow rod 810 and hand-hold rod 814 to slide through their respective clamps 808, 812 upon the release of clamp handle 816, 818 on clamp 812. Similar clamp handles are provided on clamp 810, but are not shown in the FIG. 8.

In use, the patient is positioned on support apparatus 10 such that her lower shoulder is adjacent one of indents 200, 202, 204, 206. After the patient is positioned, one of filler sections 16, 18, 20 and 22 is lowered and the patient can allow her lower arm to drop below frame 14 of support apparatus 10. The patient then grasps hand-hold rod 814 and uses rod 814 to control her position on support apparatus 10 and to aid her in preventing any forward rotation of her body toward the mammography or biopsy devices. Should rod 814 not be in the most comfortable position for the patient to grasp, the technician assisting the patient can release clamp 808, 812 and adjust the height and location of rod 814 so it may be comfortably grasped by the patient.

In yet another embodiment of the present invention patient 32 can be repositioned with respect to biopsy apparatus 38 and mammography 36 without the need to request the patient to move themselves. This repositioning of the patient is accomplished by a means for displacing frame 14 with respect to deck support 26. Generally, the repositioning is accomplished by use of two sets of rails with the first set placed perpendicular to the second set to allow repositioning movement of frame 14 both along its longitudinal axis and laterally to its longitudinal axis. That is, the present invention allows frame 14 to move, simultaneously, in both the X-axis and the Y-axis of a plane that is parallel to the top surface 48 of deck 12.

Referring now to FIGS. 3–5, the means for displacing frame 14, which also is referred to as a means for four-way lateral movement to accomplish repositioning a patient with respect to the mammography or biopsy devices while the patient is in position on the biopsy bed will now be discussed. Bed frame 14 includes parallel rails 68 and 70 which are interconnected by plate 72. In a previous embodiment, plate 72 serves as the attachment point for deck support 26 which raises and lowers frame 14 with respect to the floor of the room. However, in the present embodiment a means for movement in the X-axis and the Y-axis 500 is now provided between plate 72 and deck support 26. This means for movement in the X-axis and the Y-axis, or means for 4-way lateral movement 500 generally is comprised of a base 502 which is attached to support 26. Base 502 provides for secure attachment of four-way movement means 500 to support 26 while providing a connection surface for track plate 504 and magnetic lock 506. Magnetic lock 506, when operating to prevent movement by 4-way movement means 500, fixes metal securing plate 72 in position with respect to base 502 to prevent with X-axis movement or Y-axis movement. Magnetic lock 506 will be discussed in detail hereinafter.

Four-way movement means 500 further is comprised of four sets of roller tracks, two upper roller tracks 508a for longitudinal horizontal movement of frame 14 with respect to deck support 26 and two of lower roller tracks 508b for lateral horizontal movement of frame 14 with respect to deck support 26. Each roller track comprises a housing member 510 and a track 512 which is seated in housing 510. Roller tracks 508 operate to allow movement of frame 14 of apparatus 10, as well as the patient 32, lying thereon, in 4 horizontal directions simultaneously by the radiologist or technician.

When magnetic brake 506 is released, the radiologist or technician can simply push frame 14, by hand, into any desired location or coordinates on either horizontal X-axis or Y-axis. Once the desired position has been achieved, the radiologist or technician resets magnetic lock 506 and frame 14 is fixed in position with respect to support 26 due to the magnetic force which now connects base 502 with plate 72. Specifically, with magnetic lock 506 released, hand pressure in the Y-axis against any portion of deck 12 will cause lateral shifting of lower track 512b (FIG. 3) within lower housing 510b (FIG. 3). Similarly, hand pressure in the X-axis against any portion of deck 12 will cause longitudinal shifting of upper track 512a (FIG. 4) within upper housing 510a (FIG. 4). Thus, the displacement of upper track 512a in upper 510a results in longitudinal displacement of frame 14 with respect to support 26 and displacement of lower track 512b in lower 510b results in lateral displacement of frame 14 with respect to support 26.

To allow support apparatus to operate in both the medical mode for mammograms and biopsies and in the X-Y movement mode, it is necessary that frame 14 be prevented from movement with respect to deck support 26 when apparatus 10 is being used in the medical mode. Magnetic lock 506 allows this transition between these modes by preventing lateral and longitudinal horizontal displacement of the table when the table is being used in the medical mode. Magnetic lock 506 comprises an electric solenoid which when energized produces a magnetic field of sufficient strength to fix together base 502 with plate 72.

It will be appreciated by those skilled in the art that alternative embodiments of this principle can be applied to the present invention by substituting precision controlled motors to effect movement in the X-axis and the Y-axis in place of the rollers and track devices described previously. The object being to achieve repositioning of the area of interest on the breast without the patient moving their body with respect to the table surface.

During the mammography and biopsy procedure, it is preferred that the patient remain as immobile as possible. However, as previously described in current circumstances of patent positioning in the decubitus position it is possible for the patient to roll forward or rearward and disturb the positioning of the breast which was indicated by the mammography. To avoid this undesirable movement an embodiment of the present invention provides a back brace or support which can be position against a patient to assist in retaining a patient in the proper, selected position for a core breast biopsy.

Referring to FIG. 1, patient 32 is shown in the left position on support apparatus 10. Patient 32 is supported in position by brace 300. Referring now to FIG. 7, brace 300 is comprised of a padded support 302 having arm 304 connected thereto by block 306 on the end of arm 304 and which is pivotally received within bracket 308 on support 302. Arm 304 is rotatably captured within two-way clamp 310. Two-way clamp 310 releasably captures arm 304 and releasably captures upright 312 to join arm 304 with upright 312. Two-way clamp 310 allows rotation of arm 304 about the vertical axis presented by upright 312. This rotation about upright 312 allows movement of arm 304 toward and away from patient 32 (FIG. 1) and permits arm 304 to be locked into position to provide close, secure and supportive contact between support 302 and the patient's upper back and shoulder area. Two-way clamp 310 also allows arm 304 to rotate about the longitudinal or horizontal axis presented by arm 304. This rotational movement of arm 304 in clamp 310 allows the top or bottom of support 302 to be moved inwardly or outwardly to conform to the position of the back and shoulder of patient 32.

Clamp 310 is designed to retain and release both arm 304 and upright 312 with a single motion. By releasing handle 316, compression of clamp 310 against arm 304 and upright 312 is simultaneously released and both arm 304 and upright 312 can be moved. Setting handle 316 compresses clamp 310 against both arm 304 and upright 312 to fix these components in the selected position. Upright 312 is secured to cross arm 78 of frame 14 by foot 314. An appropriate securing bracket is attached to sides 44 and 46 of cross arm 78 to permit attachment of brace 300 to either side of support apparatus 10.

In use, patient 32 is positioned on apparatus 10 in either the left or right decubitus position. After the patient is in the approximate proper position for the mammography and biopsy procedures, brace 300 is placed against the patient's back and upper shoulder by loosening two-way clamp 310 to allow movement of brace 300. Brace 300 is then pushed toward the patient's back and upper shoulder area and arm 304 is rotated about its longitudinal axis to provide full contact between support 302 and the patient's back and upper shoulder area. Two-way clamp is then tightened to secure brace 300 against the patient to prevent the patent from rolling-back and away from biopsy apparatus 38. If additional adjustment is required, support 302 can be pivoted on bracket 308 from more complete contact with the back and upper shoulder of patient 32.

Referring now to FIG. 6, head support 28 will be described. Head support is a cushioned pad mounted on a ridged support material such as wood, plastic, metal or other substantially rigid material. The cushioned pad is covered with a resilient material such as vinyl or leather. Prior art head supports were unable to be moved inwardly or outwardly, in the path of travel indicated by Arrow H, and could not, therefore, support of the head of a woman of short stature.

As will be appreciated by examination of FIGS. 1 and 2, a woman of shorter stature will need to have her torso positioned on support table 10 so her breasts are within opening 64 when it is presented by releasing the catch on drop panel 20 and so she may avail herself of the use of indent 206 for arm comfort. If a short woman positions herself to rest her head on a prior art head rest—which could only be positioned as is shown in FIG. 1 with respect to movement along the longitudinal axis of support apparatus 10—her shoulder would not be in position to make use of indent 206 and her breasts would be too near to support arm 54 to permit proper positioning of the mammography and biopsy apparatus. Therefore, to support the head of a shorter woman and allow her to be properly positioned on support 10 it is necessary that a head support be capable of movement along the longitudinal axis of support apparatus 10 for successful positioning of the head support under the head of the patient. The present invention accomplishes this by allowing for a range of longitudinal movement of head support 28 with respect to the apparatus securing head support 28 to frame 14.

Referring now to FIG. 6, head support 28 is shown releasably attached to end cross-channel 74 of frame 14. Head support 28 is movably secured to horizontal flange 602 which is provided with slot 604. A thumb screw 606 is inserted through slot 604 in flange 602. Thumb screw 606 is received into a threaded void (not shown) in head support 28 which permits head support 28 to be fixed into position with respect to horizontal flange 602 and slot 604 by the tightening of thumb screw 606 in the threaded void of support 28. In similar fashion head support 28 can be released for movement with respect to horizontal flange 602 and slot 604 by the untightening of thumb screw 606 in the threaded void of support 28. It will be appreciated by those skilled in the art that alternative repositionable cushion mounting means can be substituted for slot 604 and thumb screw 606. For example, a series of voids and a locking pin could be used in place of slot 604. Head support 28 would then be incrementally adjustable, from void to void, rather than the continuous adjustability provided by slot 604. It will also be appreciated that as with the prior head support devices, the present head support 28 can be vertically adjusted by the outward-biasing of spring-biased locking pin 608 to remove locking pin 608 from capture in one of locking pin voids 610 on vertical flange 612 to allow vertical movement of flange 612 within bracket 614 attached to end cross-channel 74 of frame 14.

In use, when a patient of shorter stature is positioned on support apparatus 10, the patient is placed on apparatus 10 so the patient's lower shoulder is near one of indents 200, 202, 204, 206 in spine 52. This will generally properly position the patient within the opening created when one of filler sections 16, 18, 20 and 22 is lowered. Once the patient is in proper position head support 28 can be adjusted to support the patient's head. This is accomplished by adjusting vertical flange 612, as previously described, to position head support 28 just above the surface of outer support arm 54 so head support 28 can clear outer support arm 54 during longitudinal movement. The user then releases head support 28 for longitudinal movement by untightening thumb screw 606 from capture in the threaded void of support 28. Once released, head support can be moved in the direction indicated by Arrow H to shift head support 28 inwardly and under the head of the patient. Once in position, thumb screw 606 is retightened in the threaded void of support 28. In this manner the patient of shorter stature can be properly positioned on support apparatus 10 to make use of the inventive indents and be in position for testing.

In the foregoing description, certain terms have been used for brevity, clearness and understanding; but no unnecessary limitations are to be implied therefrom beyond the requirements of the prior art, because such terms are used for descriptive purposes and are intended to be broadly construed. Moreover, the description and illustration of the inventions is by way of example, and the scope of the inventions is not limited to the exact details shown or described.

Certain changes may be made in embodying the above invention, and in the construction thereof, without departing from the spirit and scope of the invention. It is intended that all matter contained in the above description and shown in the accompanying drawings shall be interpreted as illustrative and not meant in a limiting sense.

Having now described the features, discoveries and principles of the invention, the manner in which the inventive biopsy bed is constructed and used, the characteristics of the construction, and advantageous, new and useful results obtained; the new and useful structures, devices, elements, arrangements, parts and combinations, are set forth in the appended claims.

It is also to be understood that the following claims are intended to cover all of the generic and specific features of the invention herein described, and all statements of the scope of the invention which, as a matter of language, might be said to fall therebetween.

Having thus described the invention what is claimed as new and desired to be secured by Letters Patent is as follows:

1. A method of positioning an area of interest in a patient's breast when the patient is in the decubitus position on the surface of an examination table the method comprising the steps of:

positioning the patient on an examination table surface in the decubitus position, capturing the patient's breast within a holder, identifying a location of an area of interest in the patient's breast, repositioning the surface of the examination table having the patient thereon to place said location at a desired position, said repositioning comprising the steps of:

moving the examination table surface in the X axis, moving the examination table surface in the Y axis, and setting a brake mechanism to stop table surface movement.

2. An apparatus to reposition an area of interest in a patient's breast to a selected location while the patient is on the surface of an examination table in the decubitus position comprising:

a table support, a table surface for supporting the patient thereon in the decubitus position, at least one access site in said table surface within which the patient's breast is positioned, movement means located between said support and said surface for repositioning said table surface relative to said table support.

3. The apparatus as claimed in claim 2 wherein said movement means comprises:

a first roller and track to reposition said table surface in a first direction, a second roller and track to reposition said table surface in a second direction, and brake means for locking said table surface in a selected position.

4. The apparatus as claimed in claim 2 wherein said movement means comprises:

a first motor for movement of said table surface in a first direction, and a second motor for movement of said table surface in a second direction.

5. A patient support apparatus comprising:

a deck sized for supporting an adult human thereon and having first and second longitudinally spaced ends, first and second sides and a longitudinally extending spine, said deck defining two access sites between said spine and each of said sides, wherein the access sites on the first side of the deck are located opposite the access sites on the second side of the deck and separated by said spine, a deck support for elevating said deck relative to a supporting surface, and movement means located between said deck support and said deck for repositioning said deck relative to said deck support.

6. The apparatus as claimed in claim 5 wherein said movement means comprises:

a first roller and track to reposition said deck in a first direction, a second roller and track to reposition said deck in a second direction, and brake means for locking said deck in a selected position.

7. The apparatus as claimed in claim 5 wherein said movement means comprises:

a first motor for movement of said deck in a first direction, and a second motor for movement of said deck in a second direction.

8. A method of examining a breast of a patient comprising the steps of:

providing a mammography device and a patient support apparatus, said patient support apparatus including a deck elevated above a supporting surface, said deck including first and second longitudinally spaced ends and first and second transversely spaced sides, said deck further defining at least one access site along and opening to one of said sides, said access site being sized and configured to receive the mammography device therein, positioning a patient on the deck in a decubitus position facing the mammography device, positioning the mammography device within said access site in substantially facing relationship to the patient, placing a breast of the patient in imaging relationship to said mammography device, moving said deck along a longitudinal axis of said deck or laterally to a longitudinal axis of said deck relative to a deck support to reposition the breast within said mammograph device, and obtaining a mammogram.

9. The apparatus as claimed in claim 8 wherein said movement means comprises:

a first roller and track to reposition said deck in a first direction, a second roller and track to reposition said deck in a second direction, and brake means for locking said deck in a selected position.

10. The apparatus as claimed in claim 8 wherein said movement means comprises:

a first motor for movement of said deck in a first direction, and a second motor for movement of said deck in a second direction.

11. In combination:

a mammography device including an imaging device and a second camera portion; and a patient support apparatus comprising:

a deck sized to support an adult human in a lateral decubitus position thereon, said deck including longitudinally spaced first and second ends and laterally spaced first and second sides, said first side including at least one recess therein defining a first opening complementally sized to receive said first portion of said mammography device medial to said first side, wherein a breast of the human may be positioned adjacent said opening on said first portion of said mammography device while the human is in a lateral decubitus position supported by the deck; and movement means located between said support and said deck for repositioning said deck along a longitudinal axis of said deck or laterally to a longitudinal axis of said deck relative to said deck support.

12. The apparatus as claimed in claim 11 wherein said movement means comprises:

a first roller and track to reposition said deck along a longitudinal axis of said deck, a second roller and track to reposition said deck laterally to a longitudinal axis of said deck, and brake means for locking said deck in a selected position.

13. The apparatus as claimed in claim 11 wherein said movement means comprises:

a first motor for movement of said deck along a longitudinal axis of said deck, and a second motor for movement of said deck laterally to a longitudinal axis of said deck.

* * * * *